United States Patent [19]
Malbon et al.

[11] Patent Number: 6,133,245
[45] Date of Patent: Oct. 17, 2000

[54] ANTISENSE DNA CONSTRUCTS FOR EXPRESSION OF HYBRID MRNAS DRIVEN BY INDUCIBLE, TISSUE-SPECIFIC PROMOTERS

[75] Inventors: Craig C. Malbon, Wading River; Christopher M. Moxham, Great River, both of N.Y.

[73] Assignee: The Research Foundation of State University of New York, Albany, N.Y.

[21] Appl. No.: 09/096,833

[22] Filed: Jun. 12, 1998

Related U.S. Application Data

[63] Continuation of application No. 08/543,559, Oct. 16, 1995, Pat. No. 5,858,774, which is a continuation-in-part of application No. 08/241,796, May 5, 1994, abandoned.

[51] Int. Cl.$^7$ ............................. A61K 48/00; C12P 19/34
[52] U.S. Cl. ......................... 514/44; 435/320.1; 435/325; 435/455; 536/23.1; 536/24.5; 424/93.21
[58] Field of Search ......................... 514/44; 424/93.21; 536/23.1, 24.5; 435/325, 320.1, 455, 91.1

[56] References Cited

U.S. PATENT DOCUMENTS

| | | | |
|---|---|---|---|
| 4,736,866 | 4/1988 | Leder et al. | 800/21 |
| 4,946,787 | 8/1990 | Eppstein et al. | 435/325 |
| 5,107,065 | 4/1992 | Shewmaker et al. | 800/60 |
| 5,175,383 | 12/1992 | Leder et al. | 800/21 |
| 5,175,384 | 12/1992 | Krimpenfort et al. | 800/21 |
| 5,175,385 | 12/1992 | Wagner et al. | 800/21 |
| 5,254,800 | 10/1993 | Bird et al. | 800/60 |
| 5,585,479 | 12/1996 | Hoke et al. | 536/24.5 |

FOREIGN PATENT DOCUMENTS

WO 91/16426   10/1991   WIPO.

OTHER PUBLICATIONS

Plenat (Molecular Medicine Today, vol. 1, 3, 1996, pp. 250–257).

Mullins et al. (J. Clin. Invest., vol. 98, 11, 1996, pp. S37–S40).

Branch (TIBS 23, Feb. 1998, pp. 45–50).

Crowley et al., "Phenocopy of Discoidin I–Minus Mutants by Antisense Transformation in Dictyostelium" *Cell* (1985) 43:633–641.

Rosenberg et al., "Production of Phenocopies by Krüppel Antisense RNA Injection into *Drosophila* Embryos" *Nature* (1985) 313:703–706.

Melton, "Injection Anti–Sense RNAs Specifically Block Messenger RNA Translation in vivo", *Proc. Natl. Acad. Sci. USA.* (1985) 82:144–148.

Izant and Weintraub, "Constitutive and Conditional Suppression of Exogenous and Endogenous Genes by Anti-Sense RNA" *Science* 229:345–352; 1985.

Kim and Wold, "Stable Reduction of Thymidine Kinase Activity in Cells Expressing High Levels of Anti–Sense RNA" *Cell* (1985) 42:129–138.

Izant and Weintraub, "Inhibition of Thymidine Kinase Gene Expression by Anti–Sense RNA: A Molecular Approach to Genetic Analysis" *Cell* (1984) 36:1007–1015.

Pestka et al., "Anti–mRNA: Specific Inhibition of Translation of Single mRNA Molecules" *Proc. Natl. Acad. Sci. U.S.A.* (1984) 81:7525–7528.

Mizuno et. al., "A Unique Mechanism Regulating Gene Expression: Translational Inhibition by a Complementary RNA Transcript (micRNA)" *Proc. Natl. Acad. Sci. U.S.A.* (1984) 81:1966–1970.

Coleman et al., "The Use of RNAs Complementary to Specific mRNAs to Regulate the Expression of Individual Bacterial Genes" *Cell* (1984) 37:429–436.

Weintraub et al., "Anti–sense RNA as a Molecular Tool for Genetic Analysis" *Trends in Genetics* (1985) 1:22–25.

McGarry and Lindquist, "Inhibition of Heat Shock Protein Synthesis by Heat–Inducible Antisense RNA" *Proc. Natl. Acad. Sci. U.S.A.* (1986) 83:399–403.

Watkins et al., "Regulation of the Differentiation of Teratocarcinoma Cells into Primitive Endodern by $G\alpha_{i2}$" *Science* (1992) 258:1373–1375.

San, H. et al., "Safety and Short Term Toxicity of a Novel and Cationic Formulation for Human Gene Therapy" *Human Gene Therapy* (1993) 781–788.

Christofferson, R. et al., "Ribozymes as Human Therapeutic Agents" *Journal of Medicinal Chemistry* (1994) 1012–2037.

Stull, R. et al., "Antigene, Ribozyme, and Aptomer Nucleic Acid Drugs: Progress and Prospects" *Pharmaceuticals Research* (1995).

Moxham et al., "Gi alpha 2 Mediates the Inhibitory Regulation of Adenylylcyclase in vivo: Analysis in Transgenic Mice with Gi alpha 2 Suppressed by Inducible Antisense RNA" *Developmental Genetics* (1993) 14.

Mulligan, "The Basic Science of Gene Therapy" *Science* (1993) 260; 926–932.

(List continued on next page.)

*Primary Examiner*—Scott D. Priebe
*Assistant Examiner*—Dave Trong Nguyen
*Attorney, Agent, or Firm*—Hoffmann & Baron, LLP

[57] ABSTRACT

A gene is regulated by introducing into a cell an inducible, tissue-specific antisense DNA construct. The antisense DNA construct comprises any inducible, tissue-specific gene, into which a DNA sequence antisense to any DNA sequence of the gene targeted for regulation has been inserted. The inducible, tissue-specific antisense DNA construct transcribes a hybrid messenger RNA containing an RNA sequence antisense to a sequence of the messenger RNA of the gene targeted for regulation. The hybrid messenger RNA also contains the RNA sequence of the inducible, tissue-specific gene. Some examples of suitable inducible genes include those selected from the group consisting of mammalian cytosolic phosphoenolpyruvate carboxykinase (PEPCK) (GTP, EC 4.1.1.32), mammalian atrial natriuretic factor (ANF), and mammalian alpha myosin heavy chain ($\alpha$-MHC). In a preferred embodiment, the inducible, tissue-specific gene is the rat PEPCK gene.

7 Claims, 10 Drawing Sheets

OTHER PUBLICATIONS

James, "Towards Gene Inhibition Therapy: A Review of Progress and Prospects in the Field of Antiviral Antisense Nucleic Acids and Ribozymes" *Antiviral Chemistry and Chemotherapy* (1991) 2(4): 191–214.

Uhlmann et al., "Antisense Oligonucleotides: A New Therapeutic Principle" *Chemical Reviews* (1990) 90(4);543–584.

Weiss, "Upping the Antisense Ante, Scientist Bet on Profits from Reverse Genetics" *Science News* (1991) 139:108–109.

Gewirtz et al., "Facilitating Oligonucleotide Delivery: Helping Antisense Deliver on its Promise" *Proc. Natl. Acad. Sci.* (1996) 93:3161–3163.

Orkin et al., Report and Recommendations of the Panel to Assess the NIH Investment in Research on Gene Therapy (1995) 1–41; and.

Caskey, "Antisense and Differentiation" *Annals of the New York Academy of Sciences* (1992) 660:154–158.

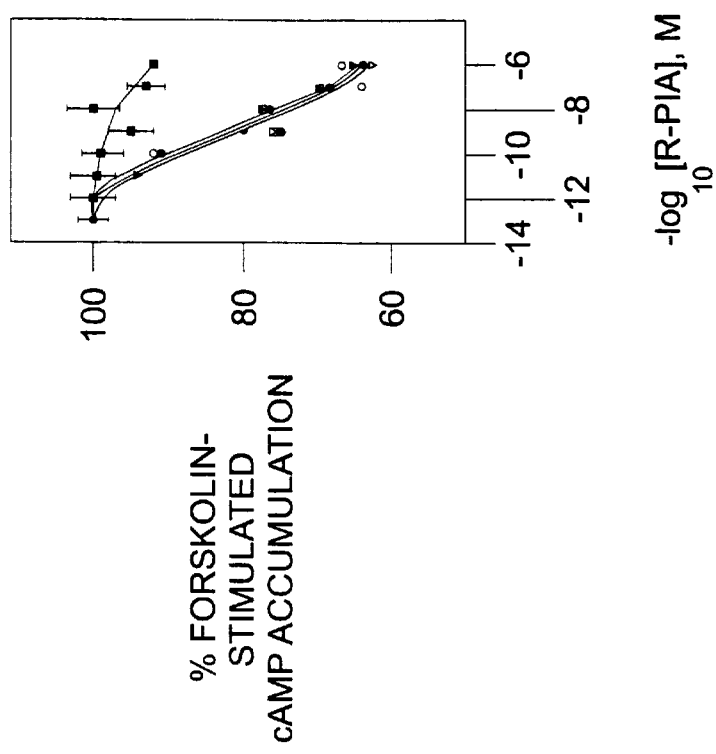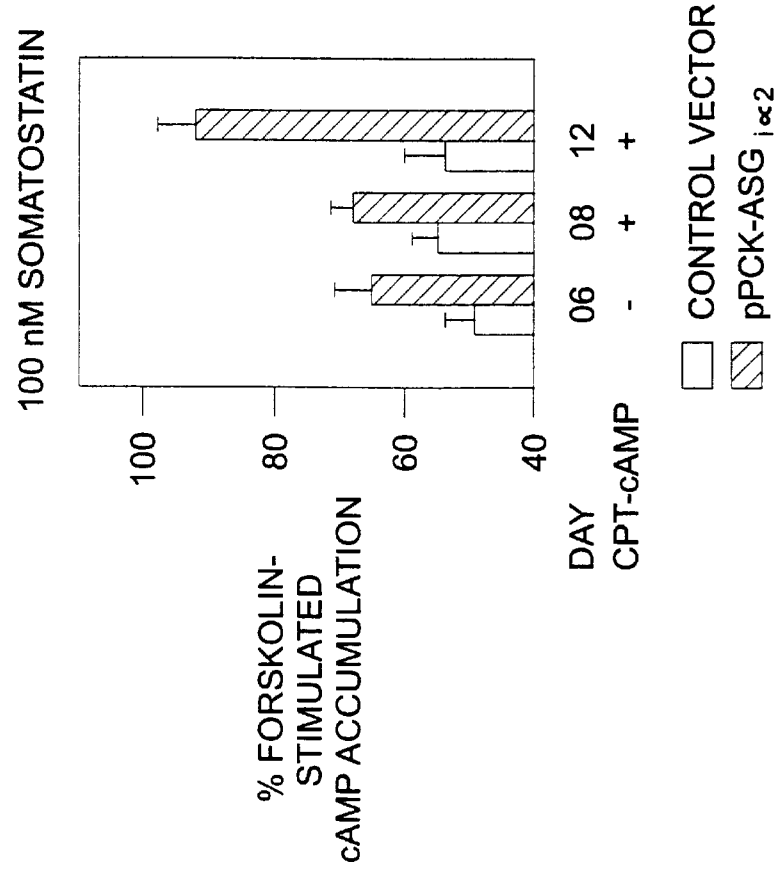
FIG-2B
FIG-2A

BDF1 CONTROL

TRANSGENIC

ANTISENSE DNA CONSTRUCTS FOR EXPRESSION OF HYBRID MRNAS DRIVEN BY INDUCIBLE, TISSUE-SPECIFIC PROMOTERS

This application is a continuation of Ser. No. 08/543,559 filed Oct. 16, 1995, now U.S. Pat. No. 5,858,774; which is a continuation-in-part of Ser. No. 08/241,796 filed May 5, 1994, now abandoned, the contents of both of which are incorporated herein by reference.

BACKGROUND OF THE INVENTION

This invention was made with Government support under Grant No. NIDDK 30111 awarded by National Institute of Diabetes, Digestive and Kidney Disorders. The Government has certain rights in the invention.

The present invention relates to the regulation of a gene product. In particular, a gene product is regulated by an inducible, tissue-specific expression vector that produces an antisense RNA sequence to the messenger RNA (mRNA) of the gene product targeted for regulation.

It is well known that a cell manufactures protein by transcribing the DNA of the gene for that protein. In particular, one of the strands of DNA of the gene is transcribed by an enzyme, RNA polymerase, to produce mRNA. The mRNA molecule has a base sequence that is complementary to that of the transcribed DNA strand. The mRNA is then processed by the removal of introns. The base sequence of the mRNA is translated into the amino acid sequence of a protein molecule by means of the genetic code. This translation process requires many enzymes and a set of transfer RNA (tRNA) molecules, which align the amino acids according to the codon sequence. The translation of mRNA into protein occurs on ribosomes. The translated protein is called a gene product.

The normal development and functioning processes of cells and organisms require that the gene products necessary to carry out these processes are available in the appropriate amounts and at the appropriate times. For example, certain gene products must be present in all cells for many fundamental physiological processes to occur. Other gene products have tissue-specificity and are only necessary in certain cells or tissues. Some gene products are continuously present either in all cells or in certain cells or tissues. Still other gene products are required at different times during development.

Gene regulation alters the quantity or quality of a gene product. These alterations can be used to ascertain the molecular activities of the normal gene product counterpart. Additionally, gene regulation can be used to manipulate cells and organisms at the genetic level. Gene regulation provides scientists and physicians with an expanded ability to study and treat disease processes. In particular, gene regulation techniques have proven especially useful in the elucidation and diagnosis of many diseases and abnormalities. It is now possible to use gene regulation for therapeutic intervention and treatment at the genetic level. In addition, gene regulation can be used to identify and characterize genes involved in fundamental embryological or cellular processes. The identification and characterization of these genes had previously been hampered by the fact that mutations in such genes are often lethal or are recessive in diploid organisms. As discussed above, the selective inactivation or regulation of genes has many potential uses.

Certain genes are regulated at the level of transcription. Transcriptional regulation is carried out either negatively (repressors) or positively (activators) by a protein factor. Specific protein factors regulate translation of specific mRNAs. Recently, it has become evident that RNAs are also involved in regulating the expression of specific genes.

Different approaches have attempted to regulate gene expression by selectively inactivating genes. For example, one way to regulate gene expression is to introduce into living cells, drugs or antibodies that are specific inhibitors of translation or transcription. The inhibition of translation has been efficiently carried out by antibiotics and other inhibitors of protein synthesis. Antibody neutralization and pharmacological perturbation, however, require prior preparation and/or characterization of target and inhibitor which can be time consuming. Further, in multicellular organisms it is difficult to regulate gene expression in a tissue-specific manner since many translational inhibitors are administered systemically.

Another approach to gene regulation is gene disruption. Gene disruption is accomplished using recombinant DNA techniques. It is a process of sequential elimination of both of the alleles for a particular gene. The alleles are eliminated by introducing a mutation into the gene, at the single cell stage of the organism, which renders the gene nonfunctional. Gene disruption is technically difficult and labor intensive. Many times additional genes are unintentionally disrupted. In addition, the gene products eliminated by gene disruption are not present in the organism or cell at any stage of development. This technique leads to a lethal outcome if the gene product is a protein that is necessary for development. Therefore, gene disruption cannot be used for the regulation of gene products that are necessary for normal pre-natal development.

Recently it has been discovered that complementary oligonucleotide inhibition of specific mRNAs can be used to inhibit the expression of a gene product. It is believed that complementary oligonucleotide inhibition of specific mRNAs will have many potential uses. For example, it is believed that it can be used to determine the role of a previously identified gene sequence in different tissues or related species. Further, this method could help to elucidate the function or functions of a gene without the prerequisite of identifying, isolating or characterizing the protein product. Moreover, complementary nucleotide sequences could be used to interfere with structures or activities of RNAs that are never translated. Finally, this approach may represent a general scheme for the functional analysis of cloned gene sequences.

Many approaches have attempted to utilize complementary oligonucleotide inhibition of specific mRNAs to regulate the expression of a gene product. For example, a direct biochemical intervention method that inhibits the expression of a gene product uses the microinjection of a complementary oligonucleotide to inhibit a specific mRNA. This method specifically blocks the translation of a gene's mRNA by RNA—RNA hybridization in vivo. The translation block prevents the synthesis of the gene product. In particular, it is possible to block the translation of a specific mRNA in vivo by microinjection of complementary (antisense) RNA. For instance, RNA complementary to globin mRNA was synthesized in vitro by transcription of an inverted globin cDNA clone. After injection into frog oocyte cytoplasm, the antisense globin RNA forms a hybrid with globin mRNA and selectively prevents its translation. This approach is an effective method of gene regulation. However, the injected antisense RNA molecules have a relatively short life-span before they are degraded or otherwise rendered unavailable for binding to the target mRNA. In addition, this is not a practical approach for the regulation of genes in multicellular organisms since the antisense RNA must be injected into individual cells.

Another gene regulation approach to antisense RNA inhibition of specific mRNAs uses DNA constructs directing the transcription of an antisense RNA strand. The RNA transcript has a sequence complementary to a target mRNA. The antisense RNA anneals to the mRNA and disrupts normal processing or translation. The antisense constructs can be introduced into eukaryotic cells by transfection or microinjection, and function in both transient and stable transformation assays. Antisense transcripts complementary to the target gene mRNA specifically suppress gene activity.

Conditional antisense inhibition can be accomplished with the use of hormone-inducible promoter sequences. For example, antisense DNA constructs were prepared by flipping a gene fragment of interest and inserting this sequence between a promoter and a polyadenylation site in inverse orientation. These antisense plasmids were then co-injected, co-transfected or co-transformed with normal sense DNA plasmid for the gene of interest into cells. While the gene of interest was regulated in the presence of the antisense plasmids, this approach is not amenable to adaptation for gene regulation in a multicellular organism.

Even if this approach were feasible in a multicellular organism, the induction of the antisense RNA would affect the production of the gene product in the whole organism, and not only in specific tissues or organs. This lack of tissue-specificity is problematic especially since the gene product can be necessary in some tissues. Additionally, the size of the gene fragment that is inserted into the plasmid in inverse orientation may be rather large. If the gene fragment is large, it is probable that the antisense RNA produced will have homology to more than just the target mRNA. This homology will suppress the expression of other gene products that are not targeted for regulation.

An example of the use of an antisense RNA transcript is the regulation of guanosine triphosphate-binding regulatory proteins (G proteins). G proteins are key elements in transmembrane signaling and have been implicated as regulators of more complex biological processes such as differentiation and development. G proteins propagate signals from cell surface receptors to a diverse group of effectors that includes adenylylcyclase, phospholipase C, and cation channels. Visual transduction, neuronal signaling, cell growth and differentiation, and metabolic pathways such as glycogenolysis and gluconeogenesis are mediated by way of G proteins. The G protein $G\alpha_{i2}$ has been implicated in the inhibition of adenylylcyclase and oncogenesis.

G protein-linked responses regulate many cellular processes in vivo such as the hormonal regulation of metabolic pathways such as lipolysis, glycogenolysis, and gluconeogenesis. The G proteins $G_s$ and $G_i$ regulate these pathways by altering the activity of adenylylcyclase and hence the intracellular amounts of cAMP. $G\alpha_s$ and $G\alpha_i$ have also been implicated in oncogenesis and differentiation. Constitutively active mutants of $G\alpha_s$ and $G\alpha_{i2}$ subunits have been identified in pituitary, thyroid, ovarian, and adrenal tumors. $G\alpha_s$ and $G\alpha_{i2}$ also regulate adipogenesis in mouse 3T3-L1 cells and stem cell differentiation of F9 teratocarcinoma cells into primitive endoderm.

For example, a DNA sequence having 39 bases that transcribe an RNA antisense to 39 bases of $G\alpha_{i2}$ may be used to inhibit expression of this important G protein gene. This 39 base sequence is selected for use in preparing an antisense construct to take advantage of the diversity of the nucleotide sequence in this region and to provide specificity. The pLNCX vector, which contains an ampicillin gene ($Amp^r$) and neomycin resistance ($Neo^r$) and retroviral packaging genes ($\Psi^+$) under the control of the mouse Moloney virus long terminal repeats (5' and 3' long terminal repeats), may be used. The antisense sequences are transcribed under the control of the cytomegalovirus promoter. The expression of the $G\alpha_{i2}$ antisense RNA is constitutive. The small size of the antisense sequence ensures specificity. This approach overcomes the problems associated with an antisense RNA having homology with more mRNAs than those targeted for regulation. However, since the antisense RNA is continuously produced, it is not possible to use this approach to regulate genes having gene products that are necessary at different developmental stages.

In view of the foregoing, there still exists a need for gene regulation methods that are simultaneously inducible and tissue-specific, and that utilize an antisense DNA construct transcribing an RNA sequence antisense to the mRNA of a gene product targeted for regulation.

SUMMARY OF THE INVENTION

The present invention provides a method of regulating a gene by introducing into a cell an inducible, tissue-specific antisense DNA construct. The antisense DNA construct comprises any inducible, tissue-specific gene, into which a DNA sequence antisense to any DNA sequence of the gene targeted for regulation has been inserted.

The inducible, tissue-specific antisense DNA construct transcribes a hybrid mRNA comprising an RNA sequence antisense to a sequence of the mRNA of the gene product targeted for regulation. The hybrid mRNA also contains the RNA sequence of the inducible, tissue-specific gene.

Some examples of suitable inducible genes include those selected from the group consisting of mammalian cytosolic phosphoenolpyruvate carboxykinase (PEPCK) (GTP, EC 4.1.1.32), mammalian atrial natriuretic factor (ANF), and mammalian alpha myosin heavy chain ($\alpha$-MHC). In a preferred embodiment, the inducible, tissue-specific gene is the rat PEPCK gene.

The antisense RNA transcribed by the antisense DNA constucts of the invention comprises an RNA sequence antisense to a mRNA of any gene product targeted for regulation. Some suitable gene products targeted for regulation include those selected from the group consisting of guanosine triphosphate-binding regulatory proteins (G proteins), mammalian G-protein linked receptors, mammalian protein serine/threonine kinases, and mammalian phosphatidylinositol bisphosphate-specific phospholipase C enzymes. In a preferred embodiment, the RNA sequence is antisense to the mRNA of the gene product $G\alpha_{i2}$.

The inducible, tissue-specific antisense DNA construct is introduced into a germ cell or a somatic cell by recombinant DNA methods known in the art, including transfection, transformation and microinjection. The antisense DNA construct may be introduced by means of a suitable expression vector.

The present invention also provides the antisense DNA construct incorporated into an expression vector. The antisense DNA construct may also be incorporated into a cassette.

The present invention further provides a transgenic non-human mammal. All of the germ cells and somatic cells of the transgenic non-human mammal contain the inducible, tissue-specific antisense DNA construct of the invention.

For a better understanding of the present invention, reference is made to the following description, the scope of which will be pointed out in the appended claims.

BRIEF DESCRIPTION OF THE DRAWINGS

FIG. 2A is a graphical representation of somatostatin inhibition of adenylylcyclase in cells transfected with a control vector or the pPCK-ASGα$_{i2}$ construct challenged with CPT-cAMP for 6 or 12 days.

FIG. 2B is a R-PIA dose response curve for cells transfected with a control vector or the pPCK-ASGα$_{i2}$ construct incubated with increasing concentrations of R-PIA.

DETAILED DESCRIPTION OF THE INVENTION

The antisense DNA construct of the invention transcribes a hybrid mRNA that comprises regions of the natural mRNA of an inducible, i.e. regulated, gene in order to confer stability on the hybrid mRNA. The regulated gene selected for the vector preferably can be suppressed in utero, is activated at birth in the desired tissues, and can be further induced or suppressed in vivo through the use of pharmacological agents or through dietary manipulation.

Several regulated genes are suitable for use in the antisense DNA constructs of the present invention, including mammalian cytosolic phosphoenolpyruvate carboxykinase (PEPCK) (GTP, EC 4.1.1.32), mammalian atrial natriuretic factor (ANF), and mammalian alpha myosin heavy chain (α-MHC). Depending on their specific requirements, those skilled in the art can substitute other regulated genes in the antisense DNA constructs. For example, the skilled artisan may prepare additional antisense DNA constructs depending on the tissue-specificity, inducibility and suppressibility requirements necessary for the regulation of a particular gene product. Further, the skilled artisan will also consider whether the gene product targeted for regulation is developmentally important. If the targeted gene product is developmentally important, the antisense DNA constructs may be developmentally regulated.

The DNA sequence that transcribes the particular antisense RNA is preferably inserted in the 5'-untranslated region of the regulated gene in the antisense DNA construct.

Figure 7:
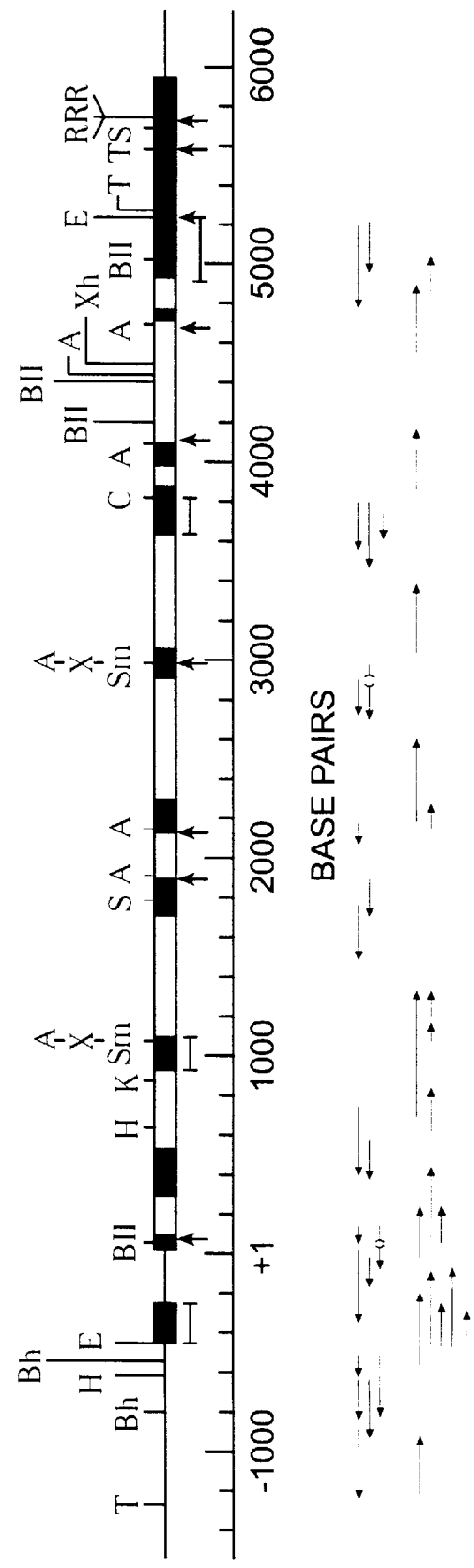
FIG. 7 is a map of the rat PEPCK gene.

In one embodiment, gene expression is suppressed in vivo by means of an antisense DNA construct comprising a DNA sequence that transcribes an antisense RNA sequence inserted in the 5'-untranslated region of the rat phosphoenolpyruvate carboxykinase (PEPCK) gene. A physical map of the rat PEPCK gene is shown in FIG. 7. Additional details regarding the PEPCK gene are reported by Beale et al., *J. Biol. Chem.*, 260: 10748–10760 (1985), which is incorporated herein by reference.

The sizes and positions of the exons and introns shown in FIG. 7 were determined by Si nuclease mapping and confirmed by sequencing. The exons are denoted by solid boxes and the introns by open boxes. The hatched box 5' of the first exon is an S1 nuclease-protected fragment that was observed but determined not to be an exon. The small vertical arrows point to the restriction enzyme sites used for S1 nuclease mapping. The bars originating from the arrows in the 3rd, 7th, and 10th exons mark the sizes and location of S1 protected fragments. The sequenced DNA fragments are shown by the horizontal arrows below the base scale. The arrow points in the direction of reading and its length corresponds to the number of bases determined from each 3' labeled end.

The mammalian PEPCK gene is the prefered inducible, tissue-specific gene for several reasons. First, a hybrid PEPCK-antisense RNA of the targeted gene product is more stable than a comparatively shorter-lived antisense RNA oligonucleotide.

In addition, the insertion of the antisense sequence within the PEPCK gene permits convenient regulated expression of the antisense sequence. PEPCK expression is, for example, regulated by several hormones including glucagon, which acts by way of cAMP, glucocorticoids, thyroid hormone, and insulin. Cyclic AMP coordinately increases the transcription rate of the PEPCK gene and the stability of the PEPCK mRNA.

Also advantageously, expression of the PEPCK gene is developmentally regulated. Transcription of the gene initiates at birth. Thus, the delaying of expression of a developmentally important antisense RNA until after birth prevents any potentially lethal outcome from suppression of the gene product in utero.

Virtually any gene product can be regulated by the antisense DNA constructs of the present invention. For example, gene products such as guanosine triphosphate-binding regulatory proteins (G proteins), mammalian G-protein linked receptors, mammalian protein serine/threonine kinases, and mammalian phosphatidylinositol bisphosphate-specific phospholipase C enzymes can be regulated by the present invention. In particular, the expression of guanosine triphosphate-binding regulatory proteins (G proteins) have been regulated by the method of the present invention.

The antisense DNA construct of the present invention can contain any oligonucleotide sequence whose transcript is antisense to the mRNA of a protein targeted for regulation. The antisense sequnse is inserted into the inducible, tissue-specific gene using recombinant DNA techniques know in the art. The ends of the construct may be modified using standard recombinant DNA techniques to ensure easy insertion into and removal from the vector.

In general, the antisense sequence will be relatively small. The relatively small size of the oligonucleotide sequence avoids homology with protein molecules that are not targeted for regulation. The lack of homology of the antisense sequence to other protein molecules can be checked against the sequences present in publicly available databases, such as the GenBank database.

In most cases, the oligonucleotide sequence will be approximately ten to one hundred bases in size. In a most preferred embodiment, the oligonucleotide sequence will be approximately 40 bases. Those skilled in the art will appreciate that virtually any gene product can be regulated in accordance with the present invention.

The use of inducible antisense RNA to suppress a specific gene product in vivo permits analysis of gene products. If these gene products are critical to normal development, their interruption by homologous recombination results in a lethal outcome in utero. By selection of an appropriate antisense DNA construct, the tissue-specificity, inducibility and suppressibility of the antisense RNA can be tailored for specific needs. The use of antisense RNA in vivo eliminates time-consuming gene disruption and breeding to homozygosity. Further, multiple gene products can be suppressed simultaneously using a single construct.

EXAMPLES

The following Examples serve to provide further appreciation of the invention but are not meant in any way to restrict the effective scope of the invention.

Example 1

THE pPCK-ASG$\alpha_{i2}$ CONSTRUCT

A 235-bp Nhe I-Sst I fragment containing the 39 nucleotides corresponding to the G$\alpha_{i2}$ antisense sequence was excised from the vector pLNC-ASG$\alpha_{i2}$. The protruding ends were made flush. The blunt-ended fragment was engineered into the first exon of the rat PEPCK gene at the Bgl II site (position +69 relative to the transcription start site) with standard recombinant DNA techniques. Prior to insertion of the antisense sequence into the Bgl II site, the rat PEPCK gene was subcloned as two separate fragments in the vector pGEM -7Zf(+); a 1.0-kb EcoR I-Hind III (−460 to +678) fragment and a 5.8-kb Hind III-Bam HI fragment (+679 to +6450). The 1.0-kb fragment contained the Bgl II insertion site. Plasmids carrying the desired orientation of the insert were selected by DNA sequencing. After insertion, the two fragments were religated with standard techniques. To discriminate between the endogenous PEPCK gene and the transgene, primers (P1, P2) were synthesized that were complementary to the flanking ends of the insert, thus permitting subsequent PCR amplification of only the 235-bp insert present in the pPCKASG$\alpha_{i2}$ construct. The sequence of the primers P1 and P2 was 5'-CGTTTAGTGAACCGTCAGA- 3' (SEQ ID NO:1), and 5'-TTGCCAAACCTACAGGTGGG- 3' (SEQ ID NO:2), respectively. The 460 bp of 5'-flanking promoter sequences within the construct contained the responsive elements necessary for the tissue-specific, hormonal, and developmental regulation of gene expression, as observed with the endogenous PEPCK gene.

Figure 1:
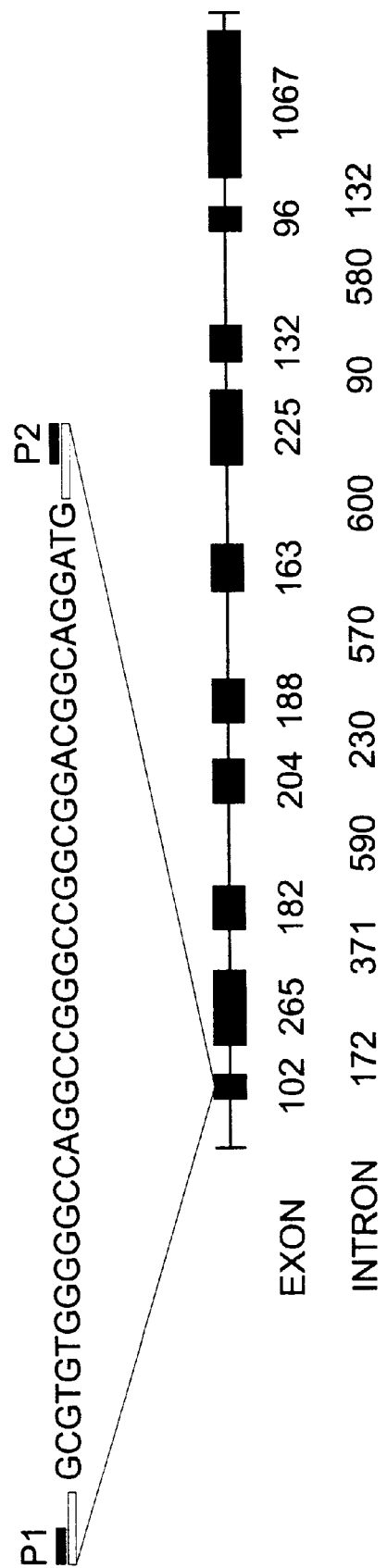
FIG. 1 is a map of the pPCK-ASGα$_{i2}$ construct.

The pPCK-ASG$\alpha_{i2}$ construct that is designed for inducible antisense RNA production is shown in FIG. 1. The 39 nucleotides immediately upstream and including the translation initiation codon (SEQ ID NO:3) were selected as the G$\alpha_{i2}$ antisense sequence because of the low degree of homology with other G protein a subunits. In addition, this sequence did not show significant homology with any of the sequences present in the GenBank database.

Example 2

ACTIVITY OF THE pPCK-ASG$\alpha_{i2}$ CONSTRUCT

The activity of the construct, shown in FIG. 1, for the expression of the G$\alpha_{i2}$ antisense RNA within the PEPCK was evaluated after transfection into FTO-2B rat hepatoma cells. Wild-type FTO-2B cells display cAMP-inducible PEPCK gene expression and express G$\alpha_{i2}$. RNA antisense to G$\alpha_{i2}$ was detected in FTO-2B clones transfected with pPCK-ASG$\alpha_{i2}$ after reverse transcription of total cellular RNA followed by polymerase chain reaction (PCR) amplification. FTO-2B clones transfected with pPCK-ASG$\alpha_{i2}$ displayed normal amounts of G$\alpha_{i2}$ expression in the absence of cAMP, an inducer of PEPCK gene expression. G$\alpha_{i2}$ expression declined >85% when the same cells were challenged with the cAMP analog, 8-(4-chlorphenylthio)-cAMP (CPT-cAMP) for 12 days. FTO-2B clones transfected with the control vector lacking the antisense sequence to G$\alpha_{i2}$ displayed no change in G$\alpha_{i2}$ expression. In contrast to the suppression of G$\alpha_2$, the steady-state amounts of G$\alpha_s$ and G$\alpha_{i3}$ were not changed in cells expressing the RNA antisense to G$\alpha_{i2}$, demonstrating that the effect of the antisense RNA expression was specific for G$\alpha_{i2}$. The time elapsing between the induction of PPCK-ASG$\alpha_{i2}$ by CPT-cAMP and the decline of steady-state amounts of G$\alpha_{i2}$ reflects the half-life of this subunit, which is about 3 days.

G$\alpha_{i2}$ is the member of the G$_i$ family most prominently implicated in mediating the inhibitory adenylylcyclase pathway. Suppression of G$\alpha_{i2}$ expression in FTO-2B cells was associated with the loss of receptor-mediated inhibition of adenylylcyclase. These results are shown in FIG. 2, A and B. In particular, the inhibition of forskolin-stimulated cAMP accumulation by either somatostatin (FIG. 2A) or the A1-purinergic agonist (−)-N$^6$-(R-phenylisopropyl)-adenosine (R-PIA, FIG. 2B) was nearly abolished in transfectant cells in which RNA antisense to G$\alpha_{i2}$ was first induced by CPT-cAMP for 12 days. The cells were treated with the indicated agonists for 15 min. at 37° C. The reaction was terminated with HCl (0.1 N final) and heating to 100° C. The amount of cAMP generated was determined with the use of a competitive binding assay described by Brown, et al., *Biochem. J.* 121: 561 (1971). FIG. 2A is a graphical representation of somatostatin inhibition of adenylylcyclase in cells transfected with the control vector or the pPCK-ASGG$\alpha_{i2}$ construct which were challenged with CPT-cAMP for 6 or 12 days. FIG. 2B is a R-PIA dose response curve. Cells transfected with the control vector (open symbols) or the pPCK-ASG$\alpha_{i2}$ construct (solid symbols) were incubated with increasing concentrations of R-PIA. Dose response curves were generated from cells cultured either in the absence (○,●) or the presence of CPT-cAMP for 6 days (◇,♦) or 12 days (□,■). The values reported are from three separate experiments performed in triplicate and are expressed as mean ±SEM. Cells transfected with the vector lacking the antisense sequence for G$\alpha_{i2}$ displayed a normal inhibitory adenylylcyclase response following a 12-day challenge with CPT-cAMP. These data demonstrate that G$\alpha_{i2}$ mediates the hormonal inhibition of hepatic adenylylcyclase.

Example 3

IN VIVO EXPRESSION OF THE pPCK-ASG$\alpha_{i2}$ CONSTRUCT

Figure 3:
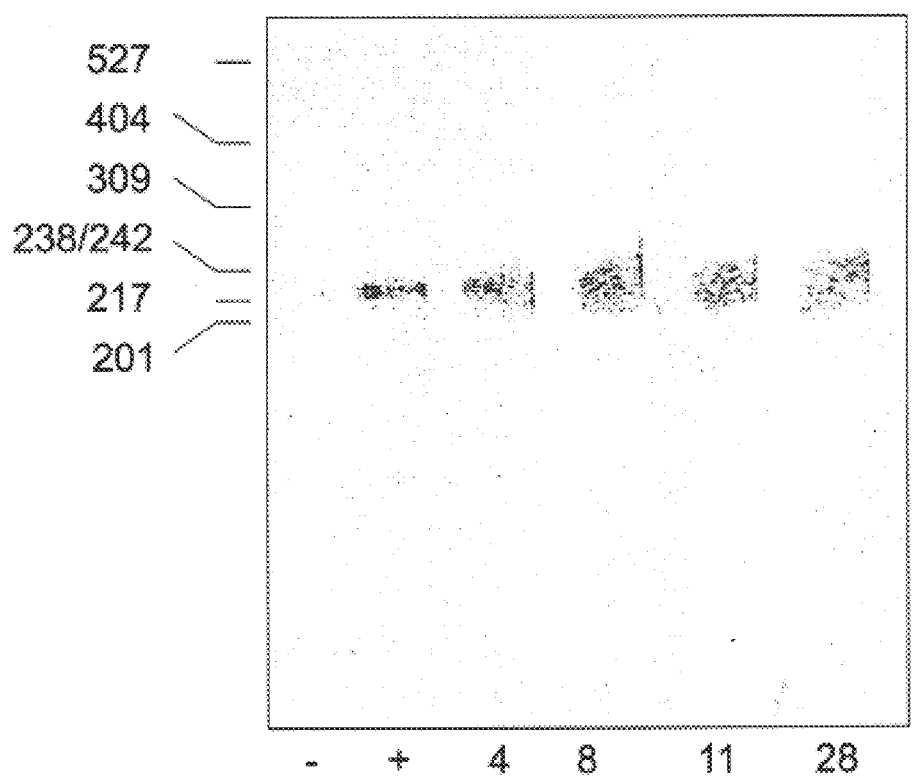
FIG. 3 is a photoradiograph of a Southern blot identifying pPCK-ASGα$_{i2}$ transgenic mice.

In vivo studies explored the consequences of G$\alpha_{i2}$ antisense RNA expression in transgenic mice. Transgenic mice were produced by methods known to those skilled in the art. The production of transgenic non-human mammals is disclosed U.S. Pat. Nos. 5,175,385, 5,175,384, 5,175,838 and 4,736,866 which are incorporated herein by reference. In particular, the pPCK-ASG$\alpha_{i2}$ construct was excised as a 7.0-kb Eco RI-Bam HI fragment free of vector sequences and microinjected into single cell, preimplantation embryos. The microinjected embryos were then transferred into pseudopregnant recipients. BDF1 mice carrying the pPCK-ASGα$_{i2}$ transgene were identified by DNA (Southern) blot analysis. These results are shown in FIG. 3. In particular, mouse tail biopsies were obtained from the offspring and genomic DNA was isolated. Of the 30 offspring, four mice were positive for the pPCK-ASGα$_{i2}$ transgene by dot-blot analysis. To confirm these results, DNA from the positive mice was subjected to PCR amplification with the primers shown in FIG. 1 and then used in Southern analysis. The PCR reaction products were separated by 4% agarose gel electrophoresis, transferred to nylon membranes, and hybridized at 65° C. with a random-primed pLNC-ASGα$_{i2}$ plasmid labeled with [$^{32}$P] dATP according to the manufacturer's protocols (Stragene). The appearance of a [32P] labeled, 0.23-kb band indicated the animal was transgenic. Lanes labeled from left to right are –(BDF1 mouse tail DNA as negative control), +(pPCK-ASGα$_{i2}$ plasmid as positive control), and mouse lines 4, 8, 11, and 28.

Four founder lines were bred and characterized over four generations. Necropsy and histology of the transgenic and control mice were performed. Epididymal fat mass was 0.27±0.01 g in control mice, but it was only 0.09±0.03 g in transgenic mice. This is a 65% decrease in fat mass after 6 weeks of neonatal growth and antisense RNA expression. The tissue weights (g) of targeted and non-targeted tissues for normal and pPCK-ASGα$_{i2}$ transgenic BDF1 mice are shown in Table 1. By 18 weeks of age, fat mass had increased in all mice, but the transgenic mice still displayed a ~60% reduction. These results are shown in Table 3. The pPCK-ASGα$_{i2}$ transgenic mice also displayed a 30% reduction in liver mass at 6 and 18 weeks of age. These results are shown in Tables 2 and 3. Inspection of a wider range of tissues and organs (Tables 1–3) indicated that growth had been diminished in tissues selectively targeted for pPCK-ASGα$_{i2}$ gene expression, i.e., in tissues that normally express PEPCK. As seen in the Tables the growth of brain, heart, lung, and skeletal muscle was unaffected in mice containing the pPCK-ASGα$_{i2}$ transgene. Kidney development was unilateral in two transgenic mice and prominent vacuolation localized to the proximal convoluted tubule of the kidney cortex was observed in 30% of all other transgenic mice. Kidney mass on average, however, was not appreciably altered.

TABLE 1

Tissue weights (g) of targeted and non-targeted tissues in normal and pPCK-ASGα$_{i2}$ transgenic BDF1 mice[1]

| Tissue | Age (6 weeks) Transgenic/normal | Ratio |
|---|---|---|
| Brain | 0.39 ± 0.01/0.44 ± 0.03 | 0.89 |
| Fat[2,3] | 0.09 ± 0.03/0.27 ± 0.03 | 0.33 |
| Heart | 0.11 ± 0.01/0.13 ± 0.01 | 0.85 |
| Kidney[2] | 0.14 ± 0.03/0.19 ± 0.02 | 0.74 |
| Liver[2] | 1.07 ± 0.08/1.49 ± 0.02 | 0.72 |
| Lung | 0.13 ± 1.01/0.15 ± 0.03 | 0.87 |
| Sk. muscle[4] | 0.10 ± 0.02/0.15 ± 0.01 | 0.67 |

[1]The results displayed are mean values ± SEM (n = 6).
[2]Denotes target tissue for pPCK-ASGα$_{i2}$.
[3]Epididymal fat pad.
[4]Gastrocnemius skeletal muscle.

TABLE 2

Tissue weights (g) of targeted and non-targeted tissues in normal and pPCK-ASGα$_{i2}$ transgenic BDF1 mice[1]

| Tissue | Age (12 weeks) Transgenic/normal | Ratio |
|---|---|---|
| Brain | 0.42 ± 0.01/0.43 ± 0.01 | 0.98 |
| Fat[2,3] | 0.19 ± 0.01/0.37 ± 0.04 | 0.49 |
| Heart | 0.14 ± 0.02/0.14 ± 0.01 | 1.00 |
| Kidney[2] | 0.19 ± 0.02/0.19 ± 0.02 | 1.00 |
| Liver[2] | 1.08 ± 0.04/1.49 ± 0.03 | 0.72 |
| Lung | 0.17 ± 1.02/0.18 ± 0.01 | 0.94 |
| Sk. muscle[4] | 0.14 ± 0.02/0.14 ± 0.02 | 1.00 |

[1]The results displayed are mean values ± SEM (n = 6).
[2]Denotes target tissue for pPCK-ASGα$_{i2}$.
[3]Epididymal fat pad.
[4]Gastrocnemius skeletal muscle.

TABLE 3

Tissue weights (g) of targeted and non-targeted tissues in normal and pPCK-ASGα$_{i2}$ transgenic BDF1 mice[1]

| Tissue | Age (18 weeks) Transgenic/normal | Ratio |
|---|---|---|
| Brain | 0.45 ± 0.02/0.46 ± 0.02 | 0.98 |
| Fat[2,3] | 0.19 ± 0.01/0.47 ± 0.01 | 0.40 |
| Heart | 0.19 ± 0.02/0.20 ± 0.02 | 0.95 |
| Kidney[2] | 0.28 ± 0.02/0.28 ± 0.03 | 1.00 |
| Liver[2] | 1.24 ± 0.03/1.89 ± 0.09 | 0.66 |
| Lung | 0.18 ± 1.02/0.19 ± 0.04 | 0.95 |
| Sk. muscle[4] | 0.20 ± 0.05/0.22 ± 0.03 | 0.91 |

[1]The results displayed are mean values ± SEM (n = 6).
[2]Denotes target tissue for pPCK-ASGα$_{i2}$.
[3]Epididymal fat pad.
[4]Gastrocnemius skeletal muscle.

Example 4

DETECTION OF pPCK-ASGα$_{i2}$ RNA

Figure 4A:
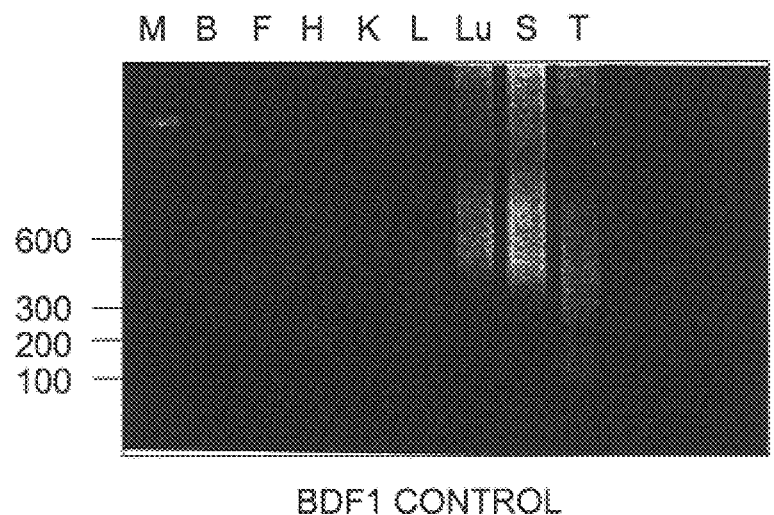
FIGS. 4A and 4B are photoradiographs of ethidium bromide agarose gels detecting pPCK-ASGα$_{i2}$ RNA expression.
Figure 4B:
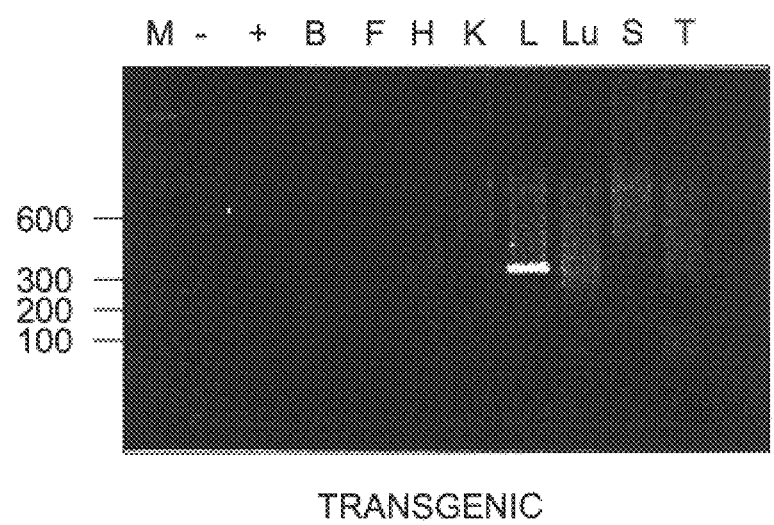

Endogenous PEPCK mRNA was detected with a probe designed to simultaneously detect and discriminate between both the pPCK-AGα$_{i2}$ RNA and the endogenous PEPCK mRNA in a ribonuclease (RNAase) protection assay. However, pPCK-ASGGα$_{i2}$ RNA expression was not detected in either FTO-2B cells that were stably transfected with the pPCK-ASGα$_{i2}$ construct or in target tissues of pPCK-ASGα$_{i2}$ transgenic mice. In the transgenic mice, the amount of endogenous PEPCK mRNA in hepatic and adipose tissue was elevated compared to the controls. In RNAase protection assays, the endogenous PEPCK mRNA was shown to be induced after challenge with CPT-cAMP in FTO-2B cells stably transfected with either the control vector or the pPCK-ASGα$_{i2}$ construct. Antisense RNA expression was detected in the liver of the transgenic mice after reverse transcription and subsequent PCR amplification of liver RNA samples. In particular, as shown in FIGS. 4A and 4B the indicated tissues were isolated from control and transgenic mice and total RNA was extracted. One microgram of total RNA was reverse-transcribed according to the manufacturer's protocol (Promega) with the pPCK-ASGα$_{i2}$-specific downstream primer, P2, to prime the reverse transcription. The reverse transcription products were then PCR-amplified with the primers P1 and P2 under the following conditions for 50 cycles: 95° C. for 1 min; 60° C. for 1 min; and 72° C. for 2 min. The reaction products were loaded onto a 2% agarose gel and visualized by staining with ethidium bromide. The left panel of FIG. 4 shows the total RNA isolated from BDF1 control mice. The lanes are labeled from left to right: M, 100-bp DNA ladder (Gibco BRL); B, brain; F, fat; H, heart; K, kidney; L, liver; Lu, lung; S, spleen; and T, testes. The right panel of FIG. 4B shows the total RNA isolated from pPCK-ASG$\alpha_{i2}$ transgenic mice. Again, the lanes are labeled from left to right: M, 100-bp DNA ladder (Gibco BRL); −, negative control; +, positive control RNA (pPCK-ASG$\alpha_{i2}$ DNA transcribed in vitro); B, brain; F, fat; H, heart; K, kidney; L, liver; Lu, lung; S, spleen; and T, testes. As shown in FIGS. 4A and 4B the PCR product of the liver RNA samples comigrated with the product of the reverse transcription and PCR amplification reaction of pPCK-ASG$\alpha_{i2}$ RNA, i.e., the positive control. In contrast to the products obtained from the hepatic RNA of transgenic mice, reaction products of the reverse transcription and PCR amplification of the liver RNA samples from the BDF1 control mice did not display a product with this mobility. These results are shown in FIGS. 4A and 4B.

The RNAase protection assays indicated that the steady-state accumulation of the transgene RNA was ~100-fold lower than that of the endogenous PEPCK mRNA. Furthermore, results from RNAase protection assays demonstrate that the endogenous PEPCK mRNA is highly abundant and inducible by cAMP in both stably transfected FTO-2B cells as well as in hepatocytes and adipocytes from pPCK-ASG$\alpha_{i2}$ transgenic animals, demonstrating that the transgene does not affect endogenous PEPCK gene expression. The elevated steady-state accumulation of endogenous PEPCK mRNA that we observed in the pPCK-ASGG$\alpha_{i2}$ transgenic mice likely reflects the elevation of intracellular cAMP, secondary to the suppression of G$\alpha_{i2}$. The reduction in G$\alpha_{i2}$ amounts observed in the adipose tissue of pPCK-ASG$\alpha_{i2}$ transgenic mice was associated with a threefold elevation in basal amounts of cAMP (4.99±0.44 and 16.45±1.37 pmol per $10^5$ cells for control and transgenic mice, respectively), as well as the loss of the inhibitory adenylylcyclase response in isolated fat cells.

Example 5

G$\alpha_{i2}$ EXPRESSION IN pPCK-ASG$\alpha_{i2}$ TRANSGENIC MICE

Figure 5A:
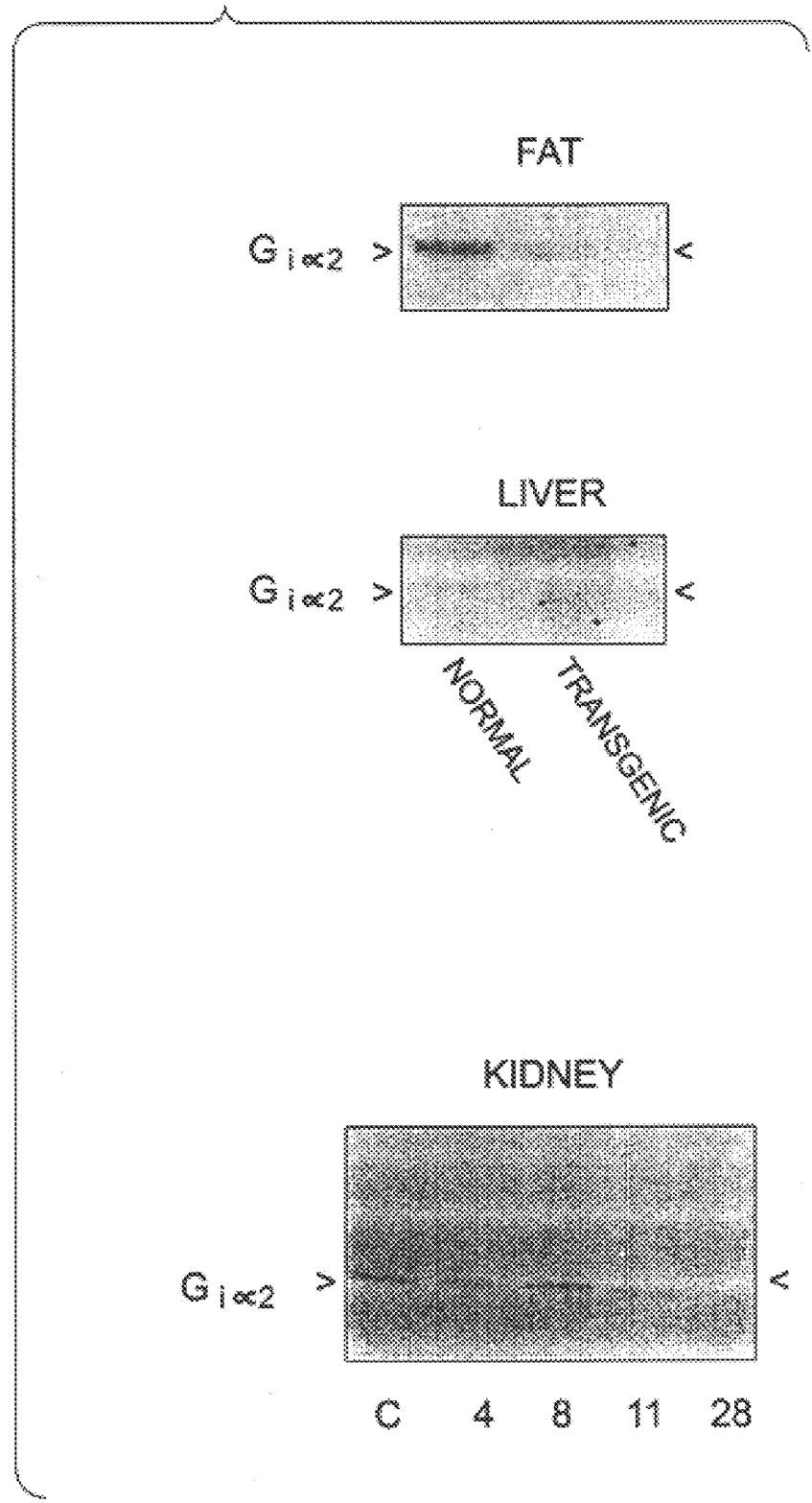
FIG. 5A is a photoradiograph of a Gα$_{i2}$ immunoblot of crude membranes (200 μg/lane) prepared from targeted tissues showing pPCK-ASGα$_{i2}$ expression.
Figure 5B:
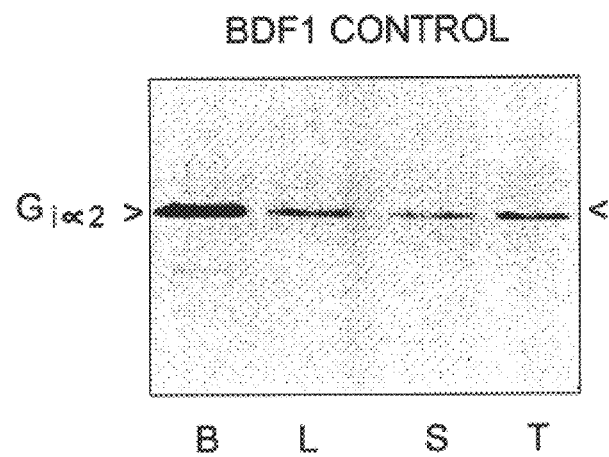
FIG. 5B is a photoradiograph of a Gα$_{i2}$ immunoblot of crude membranes (30 μg/lane) prepared from non-targeted tissues isolated from control mice.
Figure 5C:
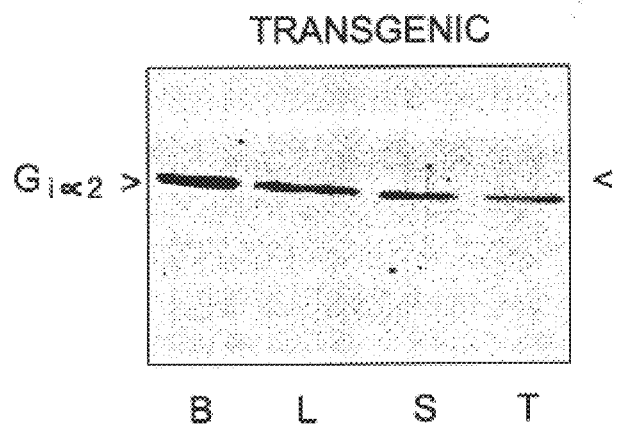
FIG. 5C is a photoradiograph of a Gα$_{i2}$ immnunoblot of crude membranes (30 μg/lane) prepared from non-targeted tissues isolated from transgenic mice.

Each of the founder mice and their transgenic offspring displayed sharply reduced G$\alpha_{i2}$ expression in tissues in which the PEPCK gene is expressed, i.e., in fat, liver, and in some cases kidney. These results are shown in FIG. 5A. In particular, crude membranes were prepared from the indicated tissues obtained from both control and transgenic mice ranging in age from 6 to 18 weeks. The samples were subjected to SDS-polyacrylamide gel electrophoresis and transferred to nitrocellulose for immunoblot analysis with antibodies specific for G$\alpha_{i2}$ (CM-112 available from Dr. Craig Malbon). FIG. 5A shows the GG$\alpha_{i2}$ immunoblot of crude membranes (200 μg/lane) prepared from targeted tissues for pPCK-ASG$\alpha_{i2}$ expression. The lanes are labeled from left to right in kidney samples: C (control BDF1) and transgenic mouse lines 4, 8, 11, and 28. The photographs shown for fat and liver samples are representative of G$\alpha_{i2}$ expression in all to the transgenic animals tested over four generations. FIGS. 5B and 5C shows the G$\alpha_{i2}$ immunoblot of crude membranes (30 μg/lane) prepared from non-targeted tissues isolated from control and transgenic mice. The lanes are labeled from left to right in each blot: B, brain; L, lung; S, spleen; and T, testes. As shown in FIG. 5B and 5C the amount of G$\alpha_{i2}$ expression was equivalent to wild type in brain, lung, spleen, and testes. The amount of G$\alpha_{i2}$ in the fat and liver of mice that express the pPCK-ASG$\alpha_{i2}$ for all four founder lines. In the kidney, the suppression of G$\alpha_{i2}$ was more variable, some animals displayed less than 5% of the control amounts, others displayed wild-type amounts of expression. The variability of G$\alpha_{i2}$ expression in the kidney may reflect epigenetic effects as a result of differences in the sites of integration of the transgene. These data indicate that G$\alpha_{i2}$ expression was suppressed in target tissues. Furthermore, albeit low relative to the amount of endogenous PEPCK mRNA, the amount of G$\alpha_{i2}$ antisense RNA that accumulated was sufficient to suppress G$\alpha_{i2}$ subunit expression.

Figure 6A:
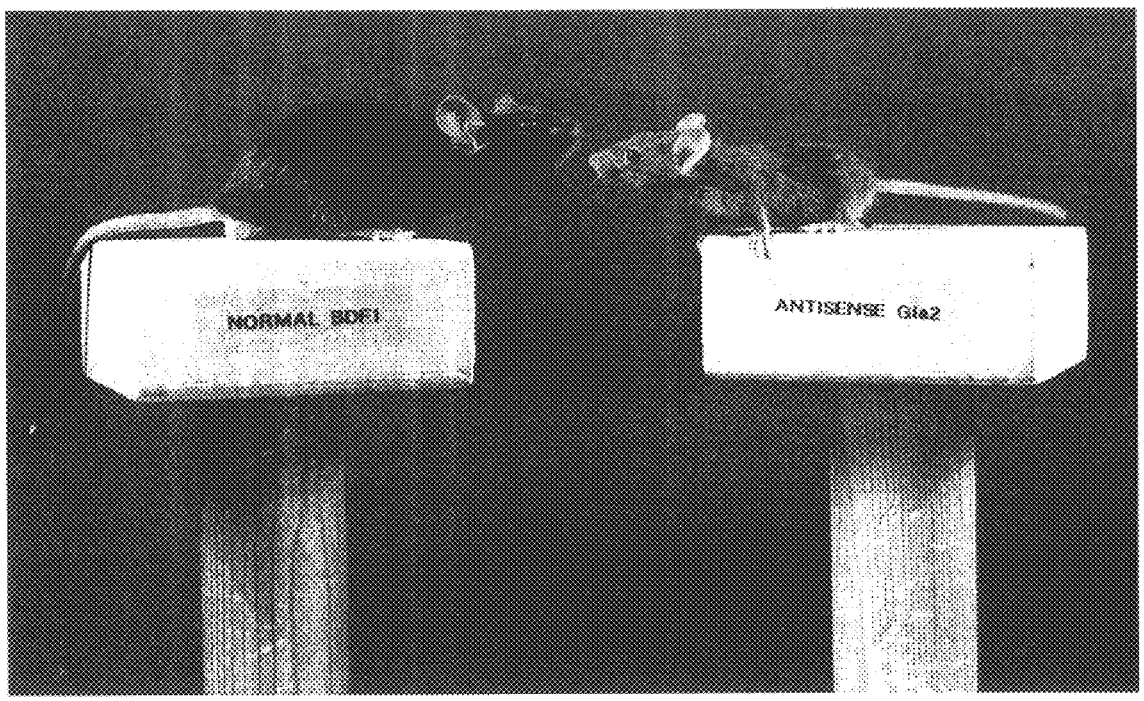
FIG. 6A is a photograph that shows that the pPCK-ASGα$_{i2}$ transgenic animals have a marked reduction in neonatal growth. Shown are control (left) and transgenic (right) male mice at 6 weeks of age.
Figure 6B:
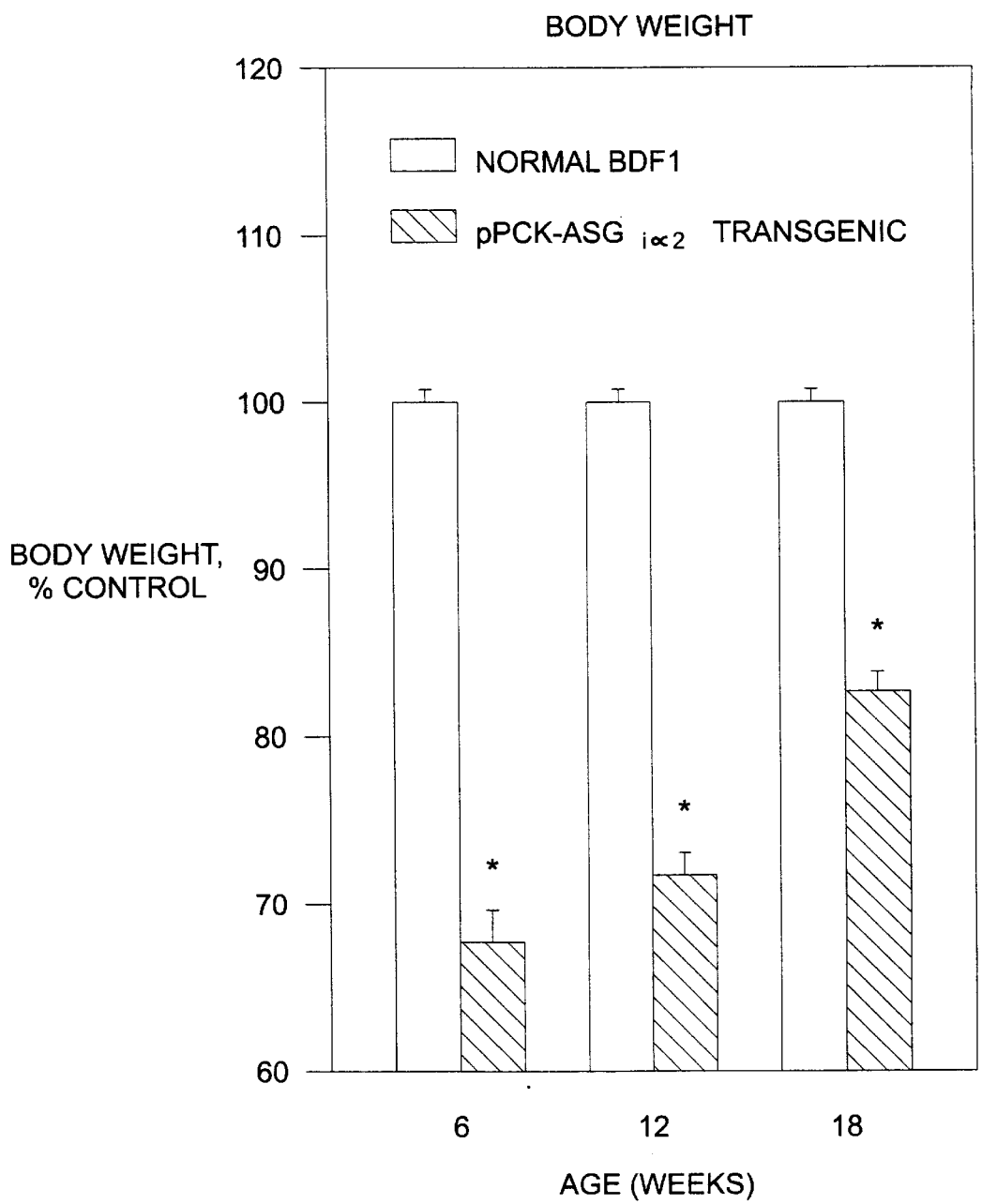
FIG. 6B is a graphical representation of normal and transgenic mice (n=6) body weights at the times indicated after birth.
Figure 6C:
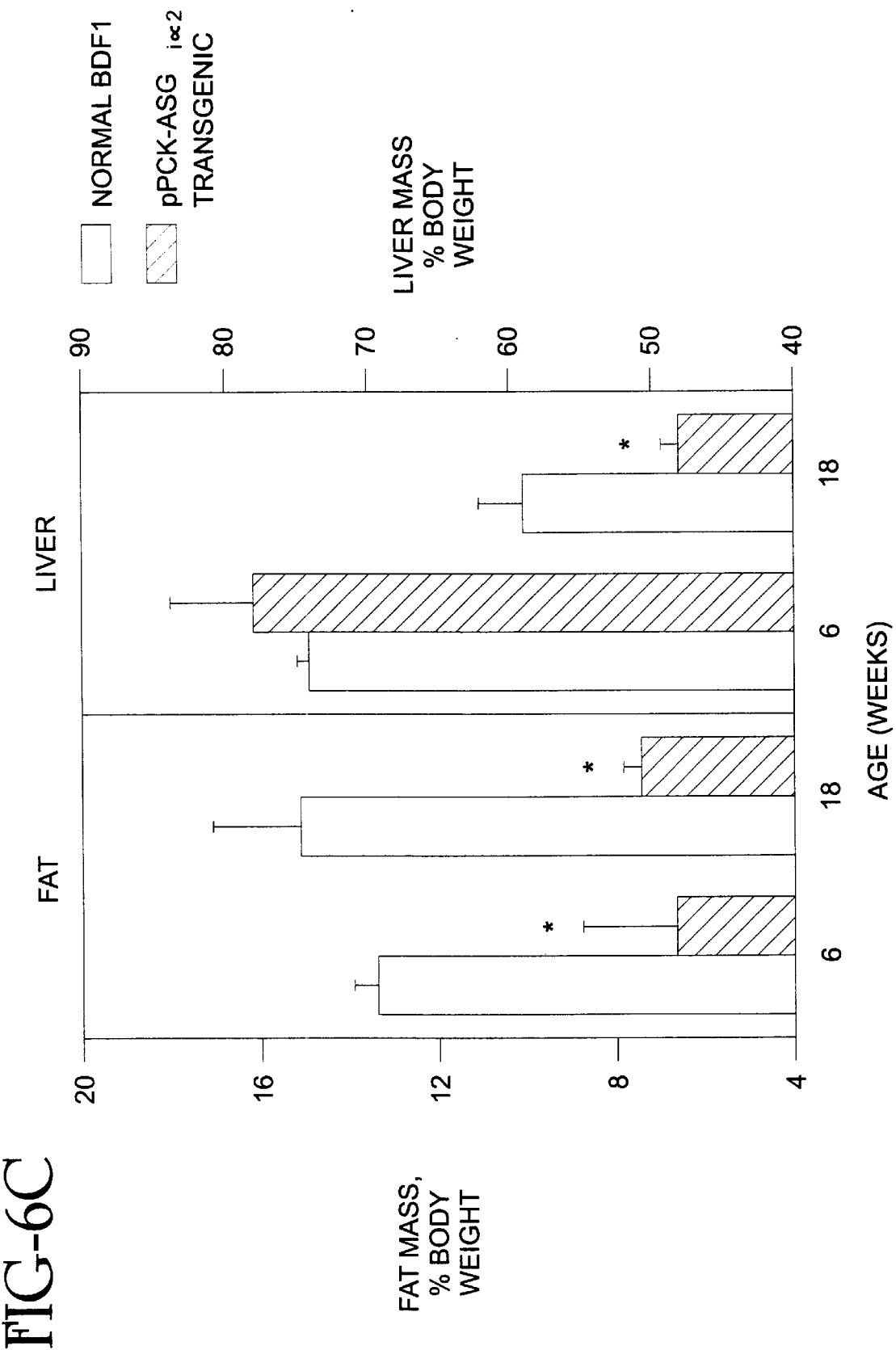
FIG. 6C is a graphical representation of fat mass and liver mass (as percent of body weight) of normal and transgenic mice (n=6) at the times indicated after birth.

As shown in FIGS. 6A and B a major characteristic of the mice carrying the pPCK-ASG$\alpha_{i2}$ transgene was a failure to thrive. Although similar to the controls at birth, after 6 weeks of postnatal development and antisense RNA expression, the transgenic mice without G$\alpha_{i2}$ displayed >30% reduction in body weight. As shown in FIG. 6A the pPCK-ASG$\alpha_{i2}$ transgenic animals have a marked reduction in neonatal growth. Shown are control (left) and transgenic (right) male mice at 6 weeks of age. The body weights of the normal and transgenic mice shown were 17 g and 9.9 g, respectively. As shown in FIG. 6B normal and transgenic mice (n=6) were weighed at the times indicated after birth. The mice were then transported to the Charles River Laboratories for complete necropsy and histological examinations of targeted and non-targeted tissues. Fat mass (expressed as percent body weight) was significantly reduced in transgenic mice at 6 and 18 weeks of age. FIG. 6C shows that liver mass (as percent of body weight) was significantly reduced in transgenic mice at 18, but not 6 weeks. The values reported are expressed as mean ±SEM. Litter size of the transgenic mice (seven to nine pups) was not significantly different from the litter size of BDF1 control mice.

Although, food consumption was equivalent for control and transgenic mice, yet the difference in body weight of transgenic mice was still observed at 18 weeks of age, and plateaued at >20% below normal at 24 weeks. As described above, FIG. 6C shows that as a percentage of body weight, fat mass was reduced in the transgenic animals lacking G$\alpha_{i2}$. Although 30% smaller in body weight at 6 weeks of age, transgenic mice had liver mass equivalent to normal mice on a percent body weight basis. By 18 weeks of age, however, transgenic mice had lower body weights than normal mice, and a liver mass considerably less (~20%) than that of the control on a percentage of body weight basis. Thus, the consequences of the loss of G$\alpha_{i2}$ on metabolic and developmental processes were observed in fat, but not liver at 6 weeks of age, whereas by 18 weeks of age the loss of G$\alpha_{i2}$ affected growth in both tissues.

What is claimed is:

1. A method for delivering to a cell an inducible, tissue-specific antisense DNA construct, the method comprising:

introducing into the cell an inducible, tissue-specific antisense DNA construct, the antisense DNA construct comprising a coding sequence of an inducible, tissue-specific gene product, into which a DNA sequence antisense to a DNA sequence of a gene targeted for regulation has been inserted, wherein the antisense DNA construct transcribes a hybrid messenger RNA that comprises:

an RNA sequence antisense to a sequence of the messenger RNA of the gene targeted for regulation; and the RNA sequence of the inducible, tissue-specific gene.

2. The method of claim 1, wherein said coding sequence of an inducible, tissue-specific gene is selected from the group consisting of mammalian cytosolic phosphoenolpyruvate carboxykinase (PEPCK), mammalian atrial natriuretic factor (ANF), and mammalian alpha myosin heavy chain (α-MHC).

3. The method of claim 1, wherein said coding sequence of an inducible, tissue-specific gene is the rat PEPCK gene.

4. The method of claim 1, wherein said gene targeted for regulation is selected from the group consisting of genes encoding guanosine triphosphate-binding regulatory proteins (G proteins), mammalian G-protein linked receptors, mammalian protein serine/threonine kinases, and mammalian phosphatidylinositol bisphosphate-specific phospholipase C enzymes.

5. The method of claim 4, wherein said gene targeted for regulation is the G protein $G\alpha_{i2}$ gene.

6. The method of claim 1, wherein said inducible, tissue-specific antisense DNA construct is introduced into said cell by a recombinant DNA method selected from the group consisting of transfection, transformation and microinjection.

7. The method of claim 1, wherein said cell is selected from the group consisting of germ cells and somatic cells.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:1:

CGTTTAGTGA ACCGTCAGA                          19

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:2:

TTGCCAAACC TACAGGTGGG                         20

(2) INFORMATION FOR SEQ ID NO:3:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:3:

GCGTGTGGGG GCCAGGCCGG GCCGGCGGAC GGCAGGATG          39